United States Patent
Wang

(10) Patent No.: US 11,649,481 B2
(45) Date of Patent: May 16, 2023

(54) METHODS AND COMPOSITIONS FOR RECOMBINASE-MEDIATED SELECTIVE CLEAVAGE OF NUCLEIC ACIDS

(71) Applicant: Illumina, Inc., San Diego, CA (US)

(72) Inventor: Clifford Lee Wang, Redwood City, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 16/609,722

(22) PCT Filed: Mar. 15, 2019

(86) PCT No.: PCT/US2019/022443
§ 371 (c)(1),
(2) Date: Oct. 30, 2019

(87) PCT Pub. No.: WO2019/182887
PCT Pub. Date: Sep. 26, 2019

(65) Prior Publication Data
US 2021/0277442 A1    Sep. 9, 2021

Related U.S. Application Data

(60) Provisional application No. 62/644,727, filed on Mar. 19, 2018.

(51) Int. Cl.
*C12Q 1/6806* (2018.01)
*C12N 15/10* (2006.01)
*C12Q 1/6844* (2018.01)

(52) U.S. Cl.
CPC ....... *C12Q 1/6806* (2013.01); *C12N 15/1003* (2013.01); *C12Q 1/6844* (2013.01)

(58) Field of Classification Search
CPC ...... C12Q 1/68; C12Q 1/6806; C12Q 1/6844; C12N 15/1003
IPC .................................................. C12Q 1/6809
See application file for complete search history.

(56) References Cited

U.S. PATENT DOCUMENTS

| | | |
|---|---|---|
| 2003/0180746 A1 | 9/2003 | Kmiec et al. |
| 2005/0112631 A1* | 5/2005 | Piepenburg ........... C12Q 1/6844 435/6.14 |
| 2011/0111409 A1* | 5/2011 | Sinicropi ............ C12Q 1/6848 435/6.11 |
| 2015/0353926 A1* | 12/2015 | Rigatti ................. C12Q 1/6806 506/2 |
| 2018/0057808 A1 | 3/2018 | Goldberg et al. |

FOREIGN PATENT DOCUMENTS

| | | | |
|---|---|---|---|
| WO | WO 2006/069346 | 6/2006 | |
| WO | WO 2008/013462 | 1/2008 | |
| WO | WO-2014020137 A1 * | 2/2014 | ........... C12Q 1/6806 |
| WO | WO 2016/100955 | 6/2016 | |

OTHER PUBLICATIONS

Longo et al., Use of uracil DNA glycosylase to control carry-over contamination in polymerase chain reactions, Gene, Sep. 1, 1990, 93, 1, 125-128. (Year: 1990).*
Riggs, Fusion Protein, Brenner's Encyclopedia of Genetics 2nd Edition, 2013, 134-135. (Year: 2013).*
Guagliardi et al., The Sso7d protein of Sulfolobus solfataricus: in vitro relationship among different activities, Archaea, 2002, 1, 7 pages. (Year: 2002).*
Briese et al: "Virome capture sequencing enables sensitive viral diagnosis and comprehensive virome analysis," MBIO, Sep. 2015, 6(5):1-11 12 pages.
Conceição-Neto et al: "Modular approach to customise sample preparation procedures for viral metagenomics: a reproducible protocol for virome analysis," Scientific Reports, Nov. 2015, 5(1):16532 14 pages.
Demidov et al: "Sequence selective double strand DNA cleavage by Peptide Nucleic Acid (PNA) targeting using nuclease S1," Nucleic Acids Research, Jan. 1993, 21 (9):2103-2107 5 pages.
Dolinšek et al: "Depletion of unwanted nucleic acid templates by selective cleavage: LNAzymes, catalytically active oligonucleotides containing locked nucleic acids, open a new window for detecting rare microbial community members," Applied and Environmental Microbiology, Dec. 2012, 79(5):1534-1544 11 pages.

* cited by examiner

*Primary Examiner* — Ethan C Whisenant
(74) *Attorney, Agent, or Firm* — Knobbe, Martens, Olson & Bear, LLP

(57) ABSTRACT

Embodiments of the methods and compositions provided herein relate to the selective cleavage of target nucleic acids. Some embodiments include recombinase-mediated selective cleavage of target nucleic acids with single-stranded nucleic acid probes and a recombinase. Some embodiments also include the enrichment of non-target nucleic acids in a sample by selective cleavage of target nucleic acids in the sample, and removal of the cleaved target nucleic acids from the sample.

20 Claims, 6 Drawing Sheets

Specification includes a Sequence Listing.

SEQUENCE LISTING

<160> NUMBER OF SEQ ID NOS: 11

<210> SEQ ID NO 1
<211> LENGTH: 196
<212> TYPE: PRT
<213> ORGANISM: Artificial Sequence
<220> FEATURE:
<223> OTHER INFORMATION: FokI variant Wild-Type

<400> SEQUENCE: 1

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 2
<211> LENGTH: 196
<212> TYPE: PRT
<213> ORGANISM: Artificial Sequence
<220> FEATURE:
<223> OTHER INFORMATION: FokI variant EL

<400> SEQUENCE: 2

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

```
Gly Gln Ala Asp Glu Met Glu Arg Tyr Val Glu Asn Gln Thr Arg
                100                 105                 110

Asn Lys His Leu Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 3
<211> LENGTH: 196
<212> TYPE: PRT
<213> ORGANISM: Artificial Sequence
<220> FEATURE:
<223> OTHER INFORMATION: FokI variant KK

<400> SEQUENCE: 3

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
                100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 4
<211> LENGTH: 196
<212> TYPE: PRT
<213> ORGANISM: Artificial Sequence
<220> FEATURE:
<223> OTHER INFORMATION: FokI variant D
```

<400> SEQUENCE: 4

```
Gln Leu Val Lys Ser Glu Leu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Asp Tyr Val Glu Asn Gln Thr Arg
            100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195
```

<210> SEQ ID NO 5
<211> LENGTH: 196
<212> TYPE: PRT
<213> ORGANISM: Artificial Sequence
<220> FEATURE:
<223> OTHER INFORMATION: FokI variant R

<400> SEQUENCE: 5

```
Gln Leu Val Lys Ser Glu Leu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Arg Glu Met Gln Arg Tyr Val Glu Asn Gln Thr Arg
            100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
    130                 135                 140
```

-continued

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 6
<211> LENGTH: 196
<212> TYPE: PRT
<213> ORGANISM: Artificial Sequence
<220> FEATURE:
<223> OTHER INFORMATION: FokI variant EA

<400> SEQUENCE: 6

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asn Lys His Ala Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 7
<211> LENGTH: 196
<212> TYPE: PRT
<213> ORGANISM: Artificial Sequence
<220> FEATURE:
<223> OTHER INFORMATION: FokI variant KV

<400> SEQUENCE: 7

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

```
Phe Met Lys Val Tyr Gly Tyr Arg Gly Lys His Leu Gly Gly Ser Arg
 50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                     85                  90                  95

Gly Gln Ala Asp Glu Met Gln Arg Tyr Val Lys Glu Asn Gln Thr Arg
                100                 105                 110

Asn Lys His Ile Asn Pro Asn Glu Trp Trp Lys Val Tyr Pro Ser Ser
                115                 120                 125

Val Thr Glu Phe Lys Phe Leu Phe Val Ser Gly His Phe Lys Gly Asn
            130                 135                 140

Tyr Lys Ala Gln Leu Thr Arg Leu Asn His Val Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
        195

<210> SEQ ID NO 8
<211> LENGTH: 196
<212> TYPE: PRT
<213> ORGANISM: Artificial Sequence
<220> FEATURE:
<223> OTHER INFORMATION: FokI variant ELD

<400> SEQUENCE: 8

Gln Leu Val Lys Ser Glu Leu Glu Glu Lys Lys Ser Glu Leu Arg His
 1                   5                  10                  15

Lys Leu Lys Tyr Val Pro His Glu Tyr Ile Glu Leu Ile Glu Ile Ala
                 20                  25                  30

Arg Asn Ser Thr Gln Asp Arg Ile Leu Glu Met Lys Val Met Glu Phe
             35                  40                  45

Phe Met Lys Val Tyr Gly Tyr Arg Gly Lys His Leu Gly Gly Ser Arg
 50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                     85                  90                  95

Gly Gln Ala Asp Glu Met Glu Arg Tyr Val Glu Glu Asn Gln Thr Arg
                100                 105                 110

Asp Lys His Leu Asn Pro Asn Glu Trp Trp Lys Val Tyr Pro Ser Ser
                115                 120                 125

Val Thr Glu Phe Lys Phe Leu Phe Val Ser Gly His Phe Lys Gly Asn
            130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
        195
```

-continued

```
<210> SEQ ID NO 9
<211> LENGTH: 196
<212> TYPE: PRT
<213> ORGANISM: Artificial Sequence
<220> FEATURE:
<223> OTHER INFORMATION: FokI variant KKR

<400> SEQUENCE: 9
```

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

```
<210> SEQ ID NO 10
<211> LENGTH: 196
<212> TYPE: PRT
<213> ORGANISM: Artificial Sequence
<220> FEATURE:
<223> OTHER INFORMATION: FokI variant Sharkey

<400> SEQUENCE: 10
```

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Pro Thr Gln Asp Arg Ile Leu Glu Met Lys Val Met Glu Phe
        35                  40                  45

Phe Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

```
Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
        195

<210> SEQ ID NO 11
<211> LENGTH: 196
<212> TYPE: PRT
<213> ORGANISM: Artificial Sequence
<220> FEATURE:
<223> OTHER INFORMATION: FokI variant Sharkey'

<400> SEQUENCE: 11

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Pro Thr Gln Asp Arg Ile Leu Glu Met Lys Val Met Glu Phe
            35                  40                  45

Leu Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly His Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly Tyr Phe Lys Gly Asp
        130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Gln
                165                 170                 175

Ala Gly Thr Leu Thr Leu Glu Glu Val Arg Arg Lys Phe Asn Asn Gly
                180                 185                 190

Glu Ile Asn Phe
        195
```

METHODS AND COMPOSITIONS FOR RECOMBINASE-MEDIATED SELECTIVE CLEAVAGE OF NUCLEIC ACIDS

CROSS-REFERENCE TO RELATED APPLICATIONS

This application is the U.S. National Phase of International App. No. PCT/US2019/022443 filed Mar. 15, 2019 which was published in English as WO 2019/182887 on Sep. 26, 2019 which claims priority to U.S. Prov. App. No. 62/644,727 filed Mar. 19, 2018 entitled "METHODS AND COMPOSITIONS FOR RECOMBINASE-MEDIATED SELECTIVE CLEAVAGE OF NUCLEIC ACIDS" which are each incorporated by reference herein in its entirety.

REFERENCE TO SEQUENCE LISTING

The present application is being filed along with a Sequence Listing in electronic format. The Sequence Listing is provided as a file entitled ILLINC408WOSEQLISTING, created Mar. 13, 2019, which is approximately 19 Kb in size. The information in the electronic format of the Sequence Listing is incorporated herein by reference in its entirety.

FIELD OF THE INVENTION

Embodiments of the methods and compositions provided herein relate to the selective cleavage of target nucleic acids. Some embodiments include recombinase-mediated selective cleavage of target nucleic acids with single-stranded nucleic acid probes and a recombinase. Some embodiments also include the enrichment of non-target nucleic acids in a sample by selective cleavage of target nucleic acids in the sample, and removal of the cleaved target nucleic acids from the sample.

BACKGROUND OF THE INVENTION

Detection of pathogens is commonly accomplished by antibody-based methods, polymerase chain reaction (PCR), or targeted nucleic acid capture followed by sequencing. Each of these approaches requires a targeting reagent, such as an antibody or DNA oligonucleotide, and thus requires prior knowledge of the pathogen. As a result, these methods can fail to detect previously undiscovered or otherwise ignored pathogens. After a pathogen of interest is identified targeted methods can be developed. However, any clinical detection or diagnostic test that includes new detection reagents requires approval by regulatory agencies, thereby increasing the cost and time to bring a test to market.

SUMMARY OF THE INVENTION

Some embodiments of the methods and compositions provided herein in a method of selectively cleaving a target nucleic acid from a non-target nucleic acid in a sample comprising: (a) obtaining a sample comprising a target nucleic acid, wherein the target nucleic acid is double-stranded; (b) contacting the target nucleic acid with a single-stranded nucleic acid probe and a recombinase such that a D-loop in the target nucleic acid is formed; and (c) contacting the D-loop with a nuclease thereby cleaving the target nucleic acid. In some embodiments, the sample comprises a non-target nucleic acid. Some embodiments also include (d) removing the cleaved target nucleic acid from the non-target nucleic acid.

In some embodiments, step (b) is performed under conditions that stabilize the D-loop. In some embodiments, step (b) comprises contacting the D-loop with a polymerase. In some embodiments, step (b) further comprises contacting the D-loop with a single-stranded binding protein.

Some embodiments also include extending the single-stranded nucleic acid probe. Some embodiments also include degrading the nucleic acid extended from the nucleic acid probe. Some embodiments also include incorporating dUTP nucleotides into the extended nucleic acid, and contacting the extended nucleic acid with a nuclease selected from the group consisting of uracil DNA glycosylase, apurinic/apyrimidinic endonuclease, and DNA glycosylase endonuclease VII.

Some embodiments also include (e) preparing a nucleic acid library comprising the non-target nucleic acid. In some embodiments, (e) is performed after step (d). In some embodiments, (e) is performed before step (b).

Some embodiments of the methods and compositions provided herein in a kit for dehosting a sample comprising a target nucleic acid and non-target nucleic acid, the kit comprising: a single-stranded nucleic acid probe; a recombinase; and a first nuclease. Some embodiments also include a component selected from the group consisting of a polymerase, a single-stranded binding protein, a terminator nucleotide, a dUTP nucleotide, and a second nuclease selected from the group consisting of uracil DNA glycosylase, apurinic/apyrimidinic endonuclease, and DNA glycosylase endonuclease VII. In some embodiments, the recombinase is selected from the group consisting of RecA, UvsX, RAD51, and derivatives thereof. In some embodiments, the first nuclease is selected from the group consisting of S1 nuclease, mung bean nuclease, and a recombinant protein comprising a domain having nuclease activity and a single-stranded nucleic acid binding domain. Some embodiments also include a plurality of single-stranded nucleic acid probes. In some embodiments, the plurality of single-stranded nucleic acid probes comprises different single-stranded nucleic acid probes.

Some embodiments of the methods and compositions provided herein in a method of removing a target RNA from a non-target RNA in a sample comprising: (a) obtaining a sample comprising a target RNA and a non-target RNA; (b) hybridizing a single-stranded DNA probe to the target RNA; (c) selectively cleaving the target RNA hybridized to the single-stranded DNA probe with a nuclease; and (d) removing the cleaved target RNA from the non-target RNA. In some embodiments, the nuclease is specific for RNA/DNA hybrids, such as RNase H.

Some embodiments of the methods and compositions provided herein in a kit for dehosting a sample comprising a target RNA and non-target RNA, the kit comprising: a single-stranded DNA probe; and a RNase H. Some embodiments also include a component selected from the group consisting of a DNase, a reverse transcriptase.

Some embodiments of the methods and compositions provided herein in a method of enriching a sample comprising a protein capsid comprising a pathogen nucleic acid for the pathogen nucleic acid, the method comprising: obtaining a sample comprising a protein capsid comprising a pathogen nucleic acid and a host nucleic acid; selectively cleaving the host nucleic acid by contacting the sample with a nuclease selected from a DNase and a RNase under conditions wherein the nuclease does not contact the pathogen nucleic acid.

DETAILED DESCRIPTION

Embodiments of the methods and compositions relate to the selective cleavage of target nucleic acids. Some embodiments include recombinase-mediated selective cleavage of target nucleic acids with single-stranded nucleic acid probes and a recombinase. Some embodiments also include the enrichment of non-target nucleic acids in a sample by selective cleavage of target nucleic acids in the sample, and removal of the cleaved target nucleic acids from the sample. In some such embodiments, target nucleic acids such as host DNA can be cleaved and removed from a sample containing the target nucleic acids and non-target nucleic acids, such as pathogen nucleic acids, thereby greatly enriching the sample for the non-target pathogen nucleic acids. This can significantly increase the sensitivity, and decrease the cost, of pathogen detection. Moreover, the methods and compositions provided here can be used to direct cleavage of a target nucleic acid at any location in the target nucleic acid.

Some embodiments include the detection of pathogen nucleic acids by unbiased sequencing. To increase the sensitivity of detection and reduce sequencing costs for an unbiased sequencing approach, one can efficiently remove host DNA from a sample. For pathogens, such as viruses that can be present at low concentrations, if one can "dehost" the blood by removing 99% of host DNA, this can increase sensitivity and reduces reagent costs by as much as 100 fold. Moreover, an unbiased nucleic acid sequencing approach can detect a pathogen without prior knowledge of the pathogen. With an unbiased sequencing approach, nucleic acids may not be enriched based on only the pathogen's genome sequence. Because any pathogen is detected based on its unique sequence, no new reagents are required. Thus little or no new regulatory approval is necessary, significantly decreasing the costs and time-to-market for clinical products. Some embodiments of the methods and compositions provided herein include selectively cleaving host DNA in a sample, removing cleaved host DNA from a sample, thereby enriching a sample for non-host nucleic acids, such as pathogen nucleic acids. Integrating such embodiments with sample preparation procedures enriches pathogen DNA so that pathogen detection can be achieved by unbiased sequencing.

Figure 1:
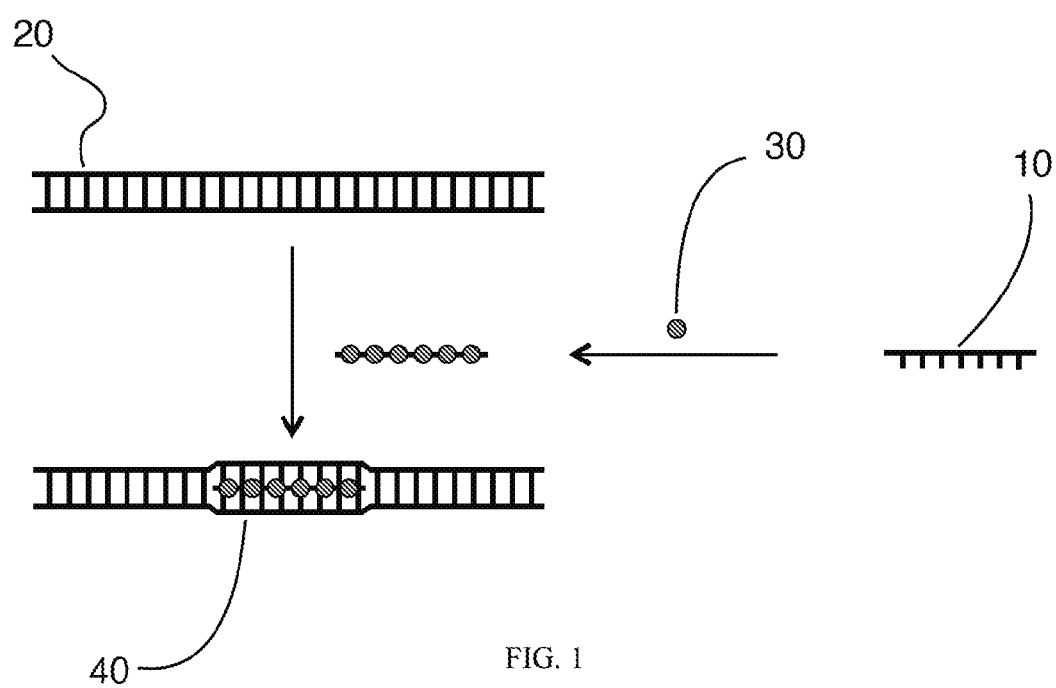
FIG. 1 depicts an example embodiment in which a target DNA is contacted with a recombinase and a single-stranded DNA probe to form a DNA triplex.

In some embodiments, a recombinase can be used to direct a single-stranded probe to a complementary sequence in a double-stranded target nucleic acid. FIG. 1 depicts an example embodiment in which a recombinase and a single-stranded DNA probe complementary to a sequence in a target DNA sequence are contacted with the target DNA sequence to form a DNA triplex, or DNA displacement loop (D-loop). Such D-loops can be primed by the probe, and then cleaved by a nuclease, such as nuclease S1 (also known as S1 nuclease). As shown in FIG. 1, a single stranded DNA 10 that is complementary to a double stranded target 20 is provided. The single stranded DNA 10 is mixed with a recombinase enzyme 30 and contacted against the double stranded target molecule 20. The recombinase enzyme 30 then forms a triple helix or D-loop 40 from the single stranded DNA 10 and the double stranded target DNA 20.

Figure 2:
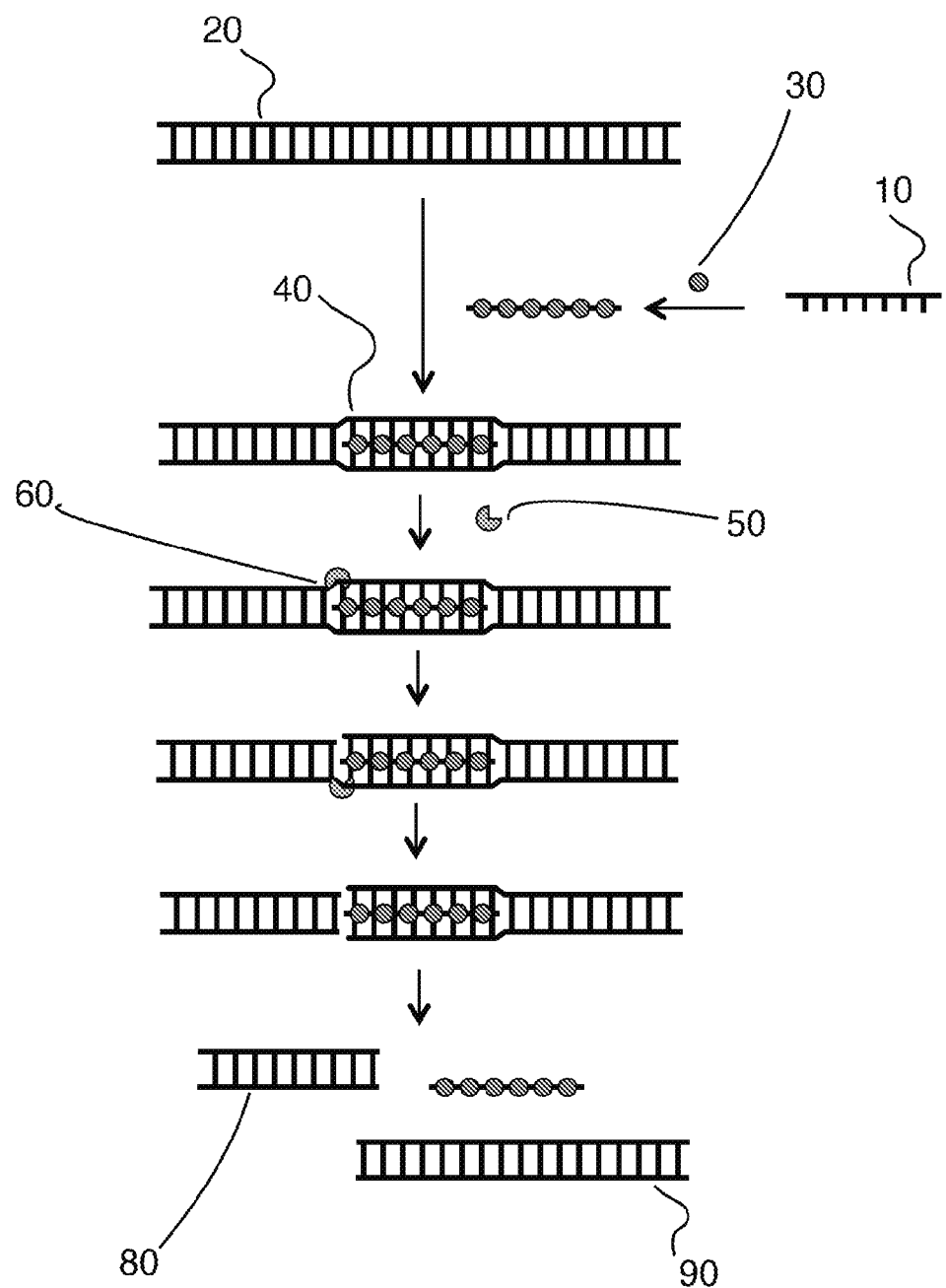
FIG. 2 depicts an example embodiment in which a host nucleic acid is selectively cleaved by recombinase-mediated cleavage.

Recombinases can deliver single-stranded DNA oligonucleotides to a double-stranded target through strand invasion. Such oligonucleotides can have a base sequence that is the same as one of the targeted DNA strands. By virtue of base complementarity to the opposite strand, the recombinase can insert the oligonucleotide into double-stranded DNA to generate a DNA triplex, a stable triple-stranded DNA structure. Recombinases capable of such strand invasion can include *E. coli* RecA and T4 UvsX. An example embodiment is depicted in FIG. 2. As shown in FIG. 2, the triple helix or D-loop 40 of FIG. 1 is contacted with a nuclease S1 50 which associates with the D-loop to form a complex 60. The nuclease S1 cleaves each strand of the double stranded target at the D-loop thereby cleaving the double-stranded DNA into fragments 80 and 90.

Figure 3:
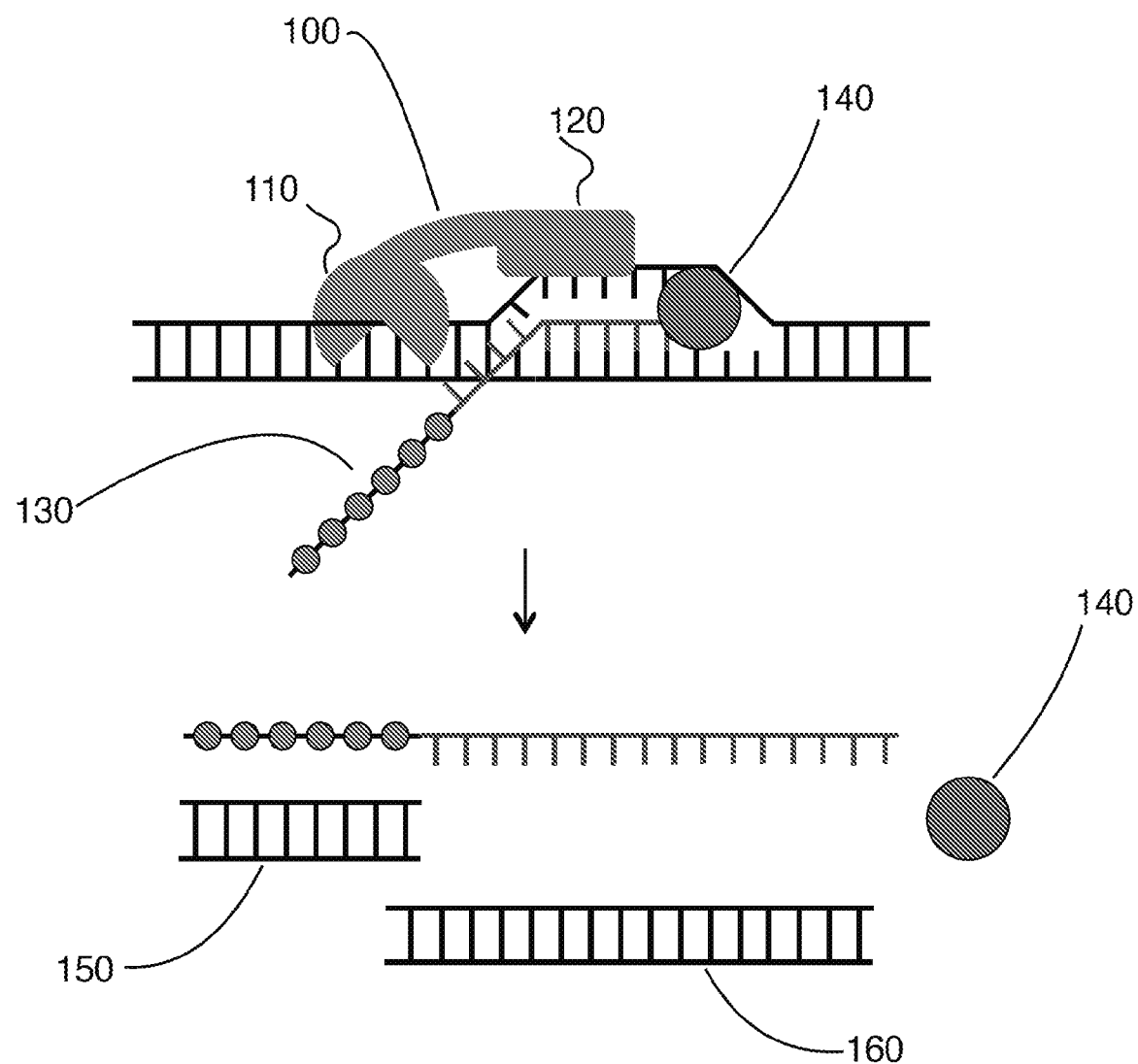
FIG. 3 depicts an example embodiment in which a recombinant protein comprising a nuclease domain and a single-stranded binding domain binds to a D-loop in which a polymerase extends a probe, and cleavage of the target nucleic acid by the recombinant protein.

Nucleases useful with embodiments provided herein include nuclease which target single-stranded DNA. Suitable nucleases include Nuclease S1 and mung bean nuclease. Nuclease S1 may also be useful since it is capable of cleaving irregularities in double-stranded structures, including those proximal to sites of strand invasion or those generated by polymerase activity that perturbs the double-helix structure. In some embodiments, a recombinant fusion protein that includes a nuclease domain and a single-stranded DNA binding domain can be used to cleave D-loop DNA and/or DNA adjacent to the D-loop. For example, a nuclease domain derived from FokI of *Flavobacterium okeanokoites*, and a single-strand binding domain derived from Sso7d of *Sulfolobus solfataricus*. As shown in FIG. 3, a recombinant protein 100 includes a single-stranded DNA binding domain 120 and a nuclease domain 110. The single-stranded DNA binding domain binds to a D-loop which has been created by a single-stranded probe DNA and recombinase complex 130. The D-loop is stabilized by a polymerase 140 extending the single-stranded probe DNA. The nuclease domain binds to double-stranded DNA adjacent to the D-loop, and cleaves the double stranded DNA into fragments 150 and 160.

Figure 4:
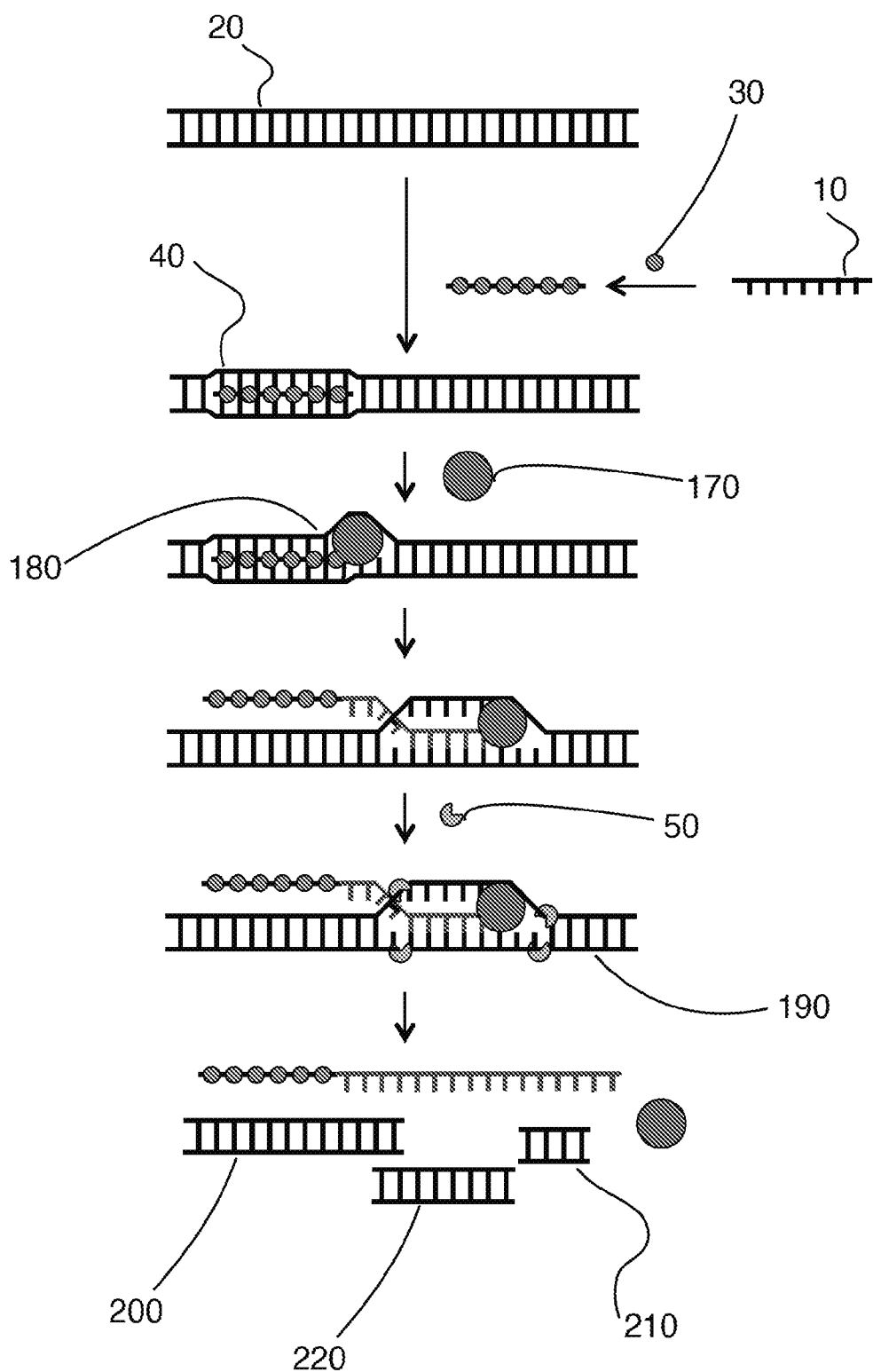
FIG. 4 depicts an example embodiment in which a host nucleic acid is selectively cleaved by recombinase-mediated cleavage in which a DNA polymerase prolongs the D-loop.

D-loops are transient structures that exist temporarily during DNA synthesis. To improve the efficiency of D-loop cleavage, various strategies can be employed to prolong D-loop existence. These strategies include variation of polymerase reaction conditions, variation of nucleotide concentrations, and the use of modified nucleotides that slow or terminate synthesis. Single-stranded binding protein may also be added to stabilize D-loops and/or newly synthesized DNA. In some embodiments, the stability of a D-loop can be increased by initiating DNA synthesis from inserted oligonucleotides probe with a polymerase. The polymerase can serve to generate and/or prolong D-loops that include the single-stranded oligonucleotides probe (strands sometimes referred to as the "sense" or "reading" strands) that is exposed during synthesis. The D-loops or DNA proximal to the D-loops can be cleaved by addition of nucleases. As shown in FIG. 4, the triple helix or D-loop 40 of FIG. 1 is contacted with a DNA polymerase 170 which binds to the D-loop to form a complex 180. The polymerase can stabilize the D-loop under conditions which extend the single-stranded probe DNA. A nuclease S1 50 can contact the D-loop stabilized by the polymerase 190, and cleave the stranded of the double-stranded host DNA to form fragments 200, 210, 220.

In some embodiments, the generation of newly synthesized DNA can be limited. Newly synthesized DNA may be limited by varying the polymerase reaction conditions, of the nucleotide concentrations, or using modified nucleotides that slow or terminate synthesis. Destruction of the newly synthesized DNA prevents the DNA from interfering in downstream processes or being sequenced later. This destruction also can expose single-stranded DNA (previously hybridized with the newly synthesized DNA) to digestion by nucleases. Degradation of the newly synthesized strand can be accomplished by incorporation of dUTP nucleotides during synthesis. The uracil-containing strand can then be cleaved by addition of uracil DNA glycosylase and apurinic/apyrimidinic endonuclease or DNA glycosylase endonuclease VII.

In an example embodiment to dehost a sample of polynucleotides containing double-stranded host DNA, and non-host pathogen nucleic acids, a recombinase and oligonucleotide probe are combined with the sample. The recombinase-activated oligonucleotide probes form D-loops in the host DNA. A polymerase and other reagents can be added to the sample to generate paused or prolonged D-loops in the host DNA. If necessary, conditions and reagents are also employed to minimize synthesis of long strands of DNA from the probes. Nuclease is added to cleave the host DNA at the D-loops, thus enriching the sample for the pathogen nucleic acids. In some embodiments, the cleaved host DNA can be removed from the sample. In some embodiments, the pathogen nucleic acids can be used to prepare a library of nucleic acids, such as a sequencing library using methods such as adapter ligation, such as TruSeq™ (Illumina, Inc., San Diego Calif.), or transposon addition, such as Nextera™ (Illumina, Inc., San Diego Calif.). In another example embodiment, a sequencing library can be prepared from a sample of polynucleotides containing double-stranded host DNA, and non-host pathogen nucleic acids, and host DNA can be selectively cleaved from the library using a recombinase, polymerase, targeting oligonucleotides, and other reagents.

In some embodiments of a dehosting application, a pool of single-stranded probes can target all or a significant portion of a target genome, such as a host genome. The single-stranded probes may be generated by chemical synthesis. Single-stranded probes may also be generated biochemically from cell lines or host tissue that do not include non-target nucleic acids, such as pathogen nucleic acids. In some such embodiments, genomic DNA is extracted from cell lines. Single-stranded probes in a range of 30-60 bases are generated from the genomic DNA. The probes can be generated using various molecular biology approaches. For example, they can be generated by use of DNase, exonuclease, and DNA size selection. Single-stranded probes may also be generated by random priming and polymerase extension; probes created by extension are then purified by standard methods. To control probe length, terminating nucleotides can be doped into the polymerization reaction mixture. Additionally, shorter probes can be created from longer single-stranded DNA by physical or biochemical fragmentation methods.

Other methods that can be used to selectively cleave target nucleic acids, such as host DNA, can include use of restriction enzymes; however, cleavage of the target nucleic acids is limited to the specific recognition sequence and restriction site for a particular restrictions enzyme. Other methods can include the use of zinc finger and transcription activator-like effector (TALE) nucleases; however, cleavage of the target nucleic acids is limited to the specific recognition sequence of the nucleases. Other methods can also include the use of CRISPR/Cas9 nuclease; however, targeting is specified by a RNA guide, chemical synthesis of such guides for host depletion would be challenging, not all host sequences can be targeted, and target sequences much include a protospacer adjacent motif (PAM).

Selective Cleavage of Target Nucleic Acids

Some embodiments include selective cleavage of one or more target nucleic acids with one or more nucleic acid probes, a recombinase and a nuclease. In some embodiments, the target nucleic acid is a double-stranded nucleic acid, and the nucleic acid probe is a single-stranded nucleic acid. In some embodiments, the target nucleic acid can include any double-stranded polynucleotide with which a recombinase and nucleic acid probe can form a D-loop. Examples of target nucleic acids include eukaryotic nucleic acids, prokaryotic nucleic acids, viral nucleic acids, synthetic nucleic acids, and cDNA. In some embodiments, a target nucleic acid can include mammalian nucleic acids, such as human nucleic acids. In some embodiments, a target nucleic acid can include genomic DNA. In some embodiments, the non-target nucleic acid can include any polynucleotide. In some embodiments, the non-target nucleic acid is not cleaved with a nuclease that cleaves a nucleic acid at D-loop or at a site proximal to a D-loop. In some embodiments, a non-target nucleic acid comprises a double-stranded polynucleotide. Examples of target nucleic acids include eukaryotic nucleic acids, prokaryotic nucleic acids, viral nucleic acids, synthetic nucleic acids, and cDNA. In some embodiments, a non-target nucleic acid comprises a polynucleotide of a pathogen.

The nucleic acid probe can contain a sequence complementary to a sequence in the target nucleic acid. In some embodiments, a nucleic acid probe can contain a sequence complementary to a target nucleic acid, such as mitochondrial DNA, a repetitive element such as an interspersed repeat, a tandem repeat, and a long terminal repeat. Some embodiments include a plurality of nucleic acid probes. In some embodiments, a plurality of nucleic probes can be complementary to sites throughout a genome. In some embodiments, a plurality of nucleic probes can be complementary to sites in a fraction of a genome. For example, nucleic acid probes can be prepared that are complementary to certain portions of a genome, such as sites within one or more chromosomes.

In some embodiments, the nucleic acid probe can have a length of at least 5 nucleotides, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, or a length in a range between any two of the foregoing lengths. In some embodiments, the nucleic acid probe can be obtained by various methods such as de novo chemical synthesis. In some embodiments, the nucleic acid probe can be obtained from genomic DNA. For example, genomic DNA can be obtained from a source, such as an organism or a cell-line. In some embodiments, the cell-line can be a somatic cell hybrid that includes one or more exogenous chromosomes. In some embodiments, the double-stranded DNA can be nicked with an enzyme such as DNase I, and the nicks can be extended to produce single-stranded gaps in the DNA with an enzyme such as exonuclease III. A library of single-stranded nucleic acid probes can be obtained from the gapped DNA by denaturing the gapped DNA, and removing the double-stranded polynucleotides. In some embodiments, genomic DNA can be used as a template to obtain a single-stranded nucleic acid probe, or library of single-stranded nucleic acid probes. For example, degenerate primers with purification tags can be used to amplify genomic DNA. The products can be purified, denatured and fragmented to provide a library of single-stranded nucleic acid probes. In some embodiments, a purification tag can include biotin which can be used with streptavidin beads to purify amplified polynucleotides from the genomic DNA. In some embodiments, the purification tag can include a poly-U sequence that can be cleaved during purification of the amplified product with an enzyme such as uracil DNA glycosylase.

Recombinases include recombinases that can catalyze hybridization of a nucleic acid probe to a strand of a target nucleic acid which is complementary to the nucleic acid probe. In some such embodiments, the recombinase can catalyze formation of a displacement loop (D-loop). A D-loop can include a structure in which the two strands of a target nucleic are separated for a certain length of nucleotides and held apart by the nucleic acid probe. In this embodiment, the nucleic acid probe has a sequence complementary to one of the target nucleic acid strands and pairs with it, thus displacing the other strand of the target nucleic acid. Examples of recombinases useful with embodiments provided herein include RecA, UvsX, RAD51, and active derivatives thereof. Examples of UvsX recombinases are provided in U.S. 2017/0275601 which is incorporated by reference in its entirety. More recombinases useful with embodiments provided herein include phage recombinases such as UvsX or UvsX-like recombinase derived from a myoviridae phage such as, for example, T4, T6, Rb69, Aeh1, KVP40, *Acinetobacter* phage 133, *Aeromonas* phage 65, cyanophage P-SSM2, cyanophage PSSM4, cyanophage S-PM2, Rb32, *Vibrio* phage nt-1, Rb16, Rb43, and Rb49. In certain embodiments, the recombinase is a UvsX or UvsX-like recombinase derived from a myoviridae phage such as, for example, T2, Rb14, *Aeromonas* phage 25, phi-1, Phage 31, phage 44RR2.8t, phage Rb3, and phage LZ2.

In some embodiments, a nuclease can be used to cleave at least one strand or both strands of the target nucleic acid at the D-loop, or at one or more sites proximate to the D-loop. Such nucleases can include endonucleases which lack any substantial sequence specificity; have activity to cleave single-stranded nucleic acids; and/or have activity to cleave one or more strands of a nucleic acid proximate to a D-loop. Examples of such nucleases include nuclease S1, and mung bean nuclease. In some embodiments, the nuclease can include a recombinant protein with a binding domain that selectively binds to single-stranded nucleic acids, such as single-stranded structures associated with a D-loop, and a nuclease domain which has activity to cleave single-stranded nucleic acids; and/or activity to cleave one or more strands of a nucleic acid proximate to a D-loop. In some embodiments, the binding domain can be derived from the DNA-binding protein 7d (Sso7d protein) of *Sulfolobus solfataricus*. In some embodiments, the nuclease domain can be derived from a FokI protein which includes an N-terminal DNA-binding domain and a non-specific DNA cleavage domain at the C-terminal; or derived from a TevI protein. In some embodiments, the FokI or fragment thereof contains a Sharkey or Sharkey' mutation, where Sharkey: S418P, K441E; and Sharkey': S418P, F432L, K441E, Q481H, H523Y, N527D, K559Q. In some embodiments, the Sharkey or Sharkey' mutation enhances the nuclease activity of the recombinant protein. In some embodiments, the nuclease domain has a mutation that renders it cold or heat sensitive. In some embodiments, the FokI or fragment thereof has one or more of the following mutations: EL, KK, D, R, EA, KV, A, V, DA, RV, REL, DKK, RELV, DKKA, ELD, KKR, KKK, ELE, DAD, RVK, DD, or RR, where EL: Q486E, I499L; KK: E490K, I538K; D: R487D; R: D483R; EA: Q486E, I499A; KV: E490K, I538V; A: I499A; V: I538V; ELD: Q486E, I499L, N496D; KKR: E490K, I538K, H537R; ELE: Q486E, I499L, N496E; KKK: E490K, I538K, H537K; KKR: E490K, I538K, H537R; DD: R487D, N496D; DAD: R487D, I499A, N496D; RR: D483R, H537R; RVR: D483R, I538V, H537R; REL: D483R, Q486E, I499L; DKK: R478D, E490K, I538K; RELV: D483R, Q486E, I499L, I538V; and DKKA: R478D, E490K, I538K, I499A.

TABLE 1 lists example FokI variants and their polypeptide sequences. In some embodiments, a nuclease domain is derived from a FokI protein or a functional fragment thereof comprises a polypeptide having identity with a polypeptide selected from SEQ ID NO:01, SEQ ID NO:02, SEQ ID NO:03, SEQ ID NO:04, SEQ ID NO:05, SEQ ID NO:06, SEQ ID NO:07, SEQ ID NO:08, SEQ ID NO:09, SEQ ID NO:10, and SEQ ID NO:11 of at least 70%, 80%, 90%, 95% or 100%, or a percentage with a range of any two of the foregoing percentages, or a conservative variation of any one of the foregoing polypeptides.

TABLE 1

| SEQ ID NO. | FokI variant | Amino acid sequence |
|---|---|---|
| 01 | Wild-Type | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMQRYVEENQTRNKHINPNEWWKV YPSSVTEFKFLFVSGHFKGNYKAQLTRLNHITNCNGAVLSVE ELLIGGEMIKAGTLTLEEVRRKFNNGEINF |
| 02 | EL | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMERYVEENQTRNKHLNPNEWWK VYPSSVTEFKFLFVSGHFKGNYKAQLTRLNHITNCNGAVLS VEELLIGGEMIKAGTLTLEEVRRKFNNGEINF |

TABLE 1-continued

| SEQ ID NO. | FokI variant | Amino acid sequence |
|---|---|---|
| 03 | KK | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMQRYVKENQTRNKHINPNEWWK VYPSSVTEFKFLFVSGHFKGNYKAQLTRLNHKTNCNGAVLS VEELLIGGEMIKAGTLTLEEVRRKFNNGEINF |
| 04 | D | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMQDYVEENQTRNKHINPNEWWKV YPSSVTEFKFLFVSGHFKGNYKAQLTRLNHITNCNGAVLSVE ELLIGGEMIKAGTLTLEEVRRKFNNGEINF |
| 05 | R | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQAREMQRYVEENQTRNKHINPNEWWKV YPSSVTEFKFLFVSGHFKGNYKAQLTRLNHITNCNGAVLSVE ELLIGGEMIKAGTLTLEEVRRKFNNGEINF |
| 06 | EA | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMERYVEENQTRNKHANPNEWWK VYPSSVTEFKFLFVSGHFKGNYKAQLTRLNHITNCNGAVLS VEELLIGGEMIKAGTLTLEEVRRKFNNGEINF |
| 07 | KV | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMQRYVKENQTRNKHINPNEWWK VYPSSVTEFKFLFVSGHFKGNYKAQLTRLNHVTNCNGAVLS VEELLIGGEMIKAGTLTLEEVRRKFNNGEINF |
| 08 | ELD | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMERYVEENQTRDKHLNPNEWWK VYPSSVTEFKFLFVSGHFKGNYKAQLTRLNHITNCNGAVLS VEELLIGGEMIKAGTLTLEEVRRKFNNGEINF |
| 09 | KKR | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMQRYVKENQTRNKHINPNEWWK VYPSSVTEFKFLFVSGHFKGNYKAQLTRLNRKTNCNGAVLS VEELLIGGEMIKAGTLTLEEVRRKFNNGEINF |
| 10 | Sharkey | QLVKSELEEKKSELRHKLKYVPHEYIELIEIARNPTQDRILEM KVMEFFMKVYGYRGEHLGGSRKPDGAIYTVGSPIDYGVIVD TKAYSGGYNLPIGQADEMQRYVEENQTRNKHINPNEWWKV YPSSVTEFKFLFVSGHFKGNYKAQLTRLNHITNCNGAVLSVE ELLIGGEMIKAGTLTLEEVRRKFNNGEINF |
| 11 | Sharkey' | QLVKSELEEKKSELRHKLKYVPHEYIELIEIARNPTQDRILEM KVMEFLMKVYGYRGEHLGGSRKPDGAIYTVGSPIDYGVIVD TKAYSGGYNLPIGHADEMQRYVEENQTRNKHINPNEWWKV YPSSVTEFKFLFVSGYFKGDYKAQLTRLNHITNCNGAVLSVE ELLIGGEMIQAGTLTLEEVRRKFNNGEINF |

In some embodiments, the nuclease domain comprises a polypeptide having identity with a polypeptide selected from SEQ ID NOs:01-11, of at least 70%, 80%, 90%, 95% or 100%, a functional fragment thereof, or a conservative variation of any one of the foregoing polypeptides. In some embodiments, a conservative amino acid variation can include an amino acid substitution that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups, for example, replacement of phenylalanine with the smaller isoleucine. Families of amino acid residues having similar side chains have been defined in the art. Several families of conservative amino acid substitutions are shown in TABLE 2.

TABLE 2

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| beta-branched | Thr, Val, Ile |
| residues that influence chain orientation | Gly, Pro |
| aromatic | Trp, Tyr, Phe, His |

In some embodiments, the efficiency of cleaving a target nucleic acid can be increased by increasing the stability of the D-loop. In some embodiments, the stability of a D-loop can be increased by contacting the D-loop with a polymerase. In some embodiments, the polymerase can extend the nucleic acid probe. Examples of reactions that can be used to extend the nucleic acid probe include an isothermal amplification reaction, or a polymerase chain reaction. The polymerase can be a DNA polymerase. In some embodiments, the conditions of the extension can be such that the rate of extension of the nucleic acid probe can be reduced, substantially inhibited, or inhibited. Examples of conditions that reduce the rate of extension of the nucleic acids probe include performing the extension in the presence of at least one type of terminator nucleotide, and performing the extension in the presence of a limiting concentration of at least one nucleotide. In some embodiments, the stability of a D-loop can be increased by contacting the D-loop with a single strand binding protein.

In some embodiments in which a polymerase extends the nucleic acid probe, the extended polynucleotide can be degraded. Degradation of the extended polynucleotide can be useful to prevent the extended polynucleotide interfering in downstream processes. In some embodiments, the nucleic acid probe can be extended in the presence of dUTP such that the extended polynucleotide includes UTP residues. The extended polynucleotide containing UTP residues can be degraded using enzymes such as uracil DNA glycosylase, apurinic/apyrimidinic endonuclease, or DNA glycosylase endonuclease VII.

Some embodiments include enriching a sample of polynucleotides for a non-target nucleic acid. In some embodiments, a sample can comprise a target nucleic acid and a non-target nucleic acid, the target nucleic acid can be selectively cleaved with a method provided herein, and the cleaved target nucleic acid can be removed from the non-target nucleic acid. In some embodiments, the cleaved target nucleic acid can be removed by methods which fractionate polynucleotides according to size. In some embodiments, methods that can be used to remove a cleaved target nucleic acid from a non-target nucleic acid include binding the non-target nucleic acid to a substrate, hybridizing the non-target nucleic acid to a capture probe, and/or performing gel filtration. In some embodiments, the substrate comprises solid phase reversible immobilization (SPRI) beads.

In some embodiments provided herein, selective cleavage of target nucleic acids in a sample of polynucleotides, and removal of the cleaved target nucleic acids can result in a sample or sequencing library that comprises, for example, at least 50%, at least 60%, at least 70%, at least 80%, at least 90%, at least 95%, at least 96%, at least 97%, at least 98%, at least 99%, or 100% non-host nucleic acids, or any range of values thereof. In some embodiments the methods result in a sample or sequencing library in which non-host nucleic acids comprise, for example, from 50% to 100%, from 60% to 100%, from 70% to 100%, from 80% to 100%, from 90% to 100%, or from 95% to 100% of the nucleic acids in the sample or sequencing library. In some embodiments the methods result in a sample or sequencing library that is enriched for non-host nucleic acids. In some embodiments, the sample or sequencing library that is enriched for non-host nucleic acids by 2×, 3×, 4×, 5×, 10×, 20×, 50×, 100×, 200×, 500×, 1000×, 10,000×, 100,000×, or 1,000,000×, compared to the starting sample.

In some embodiments, a sample can be obtained from a cell, fluid, tissue, or organ from an organism or cell-culture, such as blood, serum, plasma, tears, saliva, mucus, urine, milk, semen, muscle, heart, liver, skin, liver, kidney, or adipose tissue. In some embodiments, a sample can be from a cell-culture. In some embodiments, a sample is an environmental sample, such as a soil, water, or air sample. In some embodiments, the sample is a biological sample. In some embodiments, the sample is from a human. In some embodiments, the sample is from a non-human eukaryote. In some embodiments, the sample is from an animal. In some embodiments, the sample is from a plant. In some embodiments, the sample is from a fungus. In some embodiments, the sample is from a protozoan. In some embodiments, the sample contains nucleic acid from at least two different prokaryotic organisms. In some embodiments, the sample contains nucleic acid from human and bacterial organisms. In some embodiments, the sample contains nucleic acid from eukaryotic and prokaryotic organisms. In some embodiments, the sample contains nucleic acid from at least two different eukaryotic organisms. In some embodiments, the sample contains nucleic acid from an unknown organism.

Selective Enrichment of RNA

Figure 5:
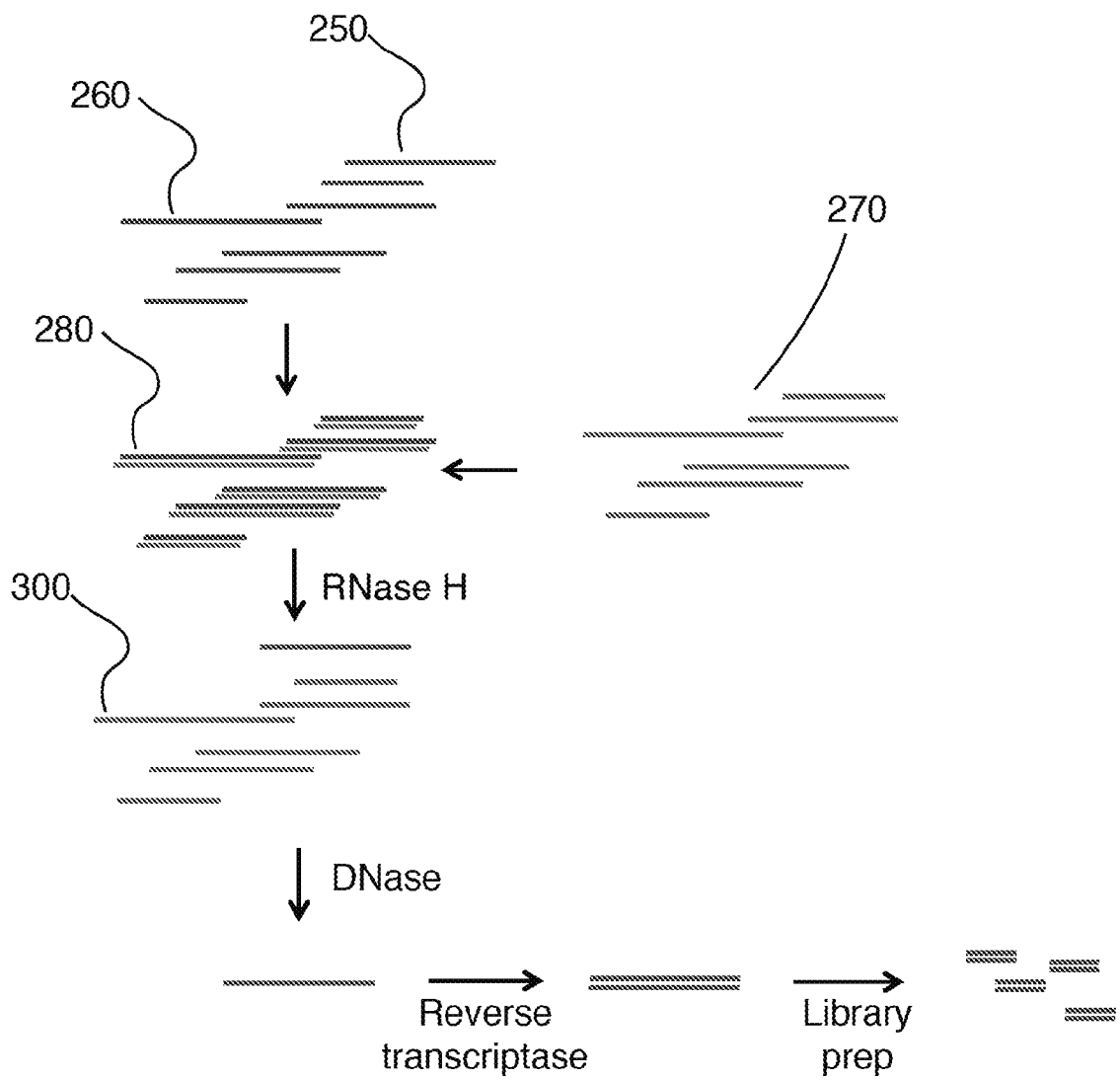
FIG. 5 depicts an example embodiment for selective enrichment of pathogen RNA in a sample that contains human host RNA and pathogen RNA.

Some embodiments include selective removal of target RNA from a sample containing the target RNA and a non-target RNA. In some embodiments, a single-stranded DNA probe is hybridized to the target RNA. In some embodiments, the single-stranded DNA probe includes a sequence complementary to a sequence selected from the group consisting of ribosomal RNA, tRNA, and mRNA. In some embodiments, a plurality of single-stranded DNA probes can be hybridized to one or more target RNAs in a sample. The single-stranded DNA probe hybridizes to the target RNA. The double-stranded RNA/DNA hybrid can be contacted with an RNase that selectively degrades RNA of a double-stranded RNA/DNA hybrid, such an RNase H. The single-stranded DNA can be degraded with a DNase. In some embodiments, the non-target RNA can be captured with method that can include binding the non-target RNA to a substrate, hybridizing the non-target RNA to a capture probe, or performing gel filtration. In some embodiments, the substrate comprises solid phase reversible immobilization (SPRI) beads. In some embodiments, the non-target RNA can be reverse transcribed. Some embodiments also include preparing a library of nucleic acids from the reversed transcribed non-target RNA. Some embodiments also include sequencing the library of nucleic acids. An example embodiment is depicted in FIG. 5 in which an RNA sample includes pathogen RNA 250 and human host RNA 260. Single-stranded DNA 270 which target host RNA can be hybridized to the RNA sample to form RNA/DNA hybrids 280 with the host RNA. The RNA strands of the RNA/DNA hybrids can be digested with RNase H, and the remaining single-stranded DNA strands 300 can be digested with DNase to leave non-targeted pathogen RNA. The RNA can be reverses transcribed and use to generate a library of nucleic acids.

Figure 6:
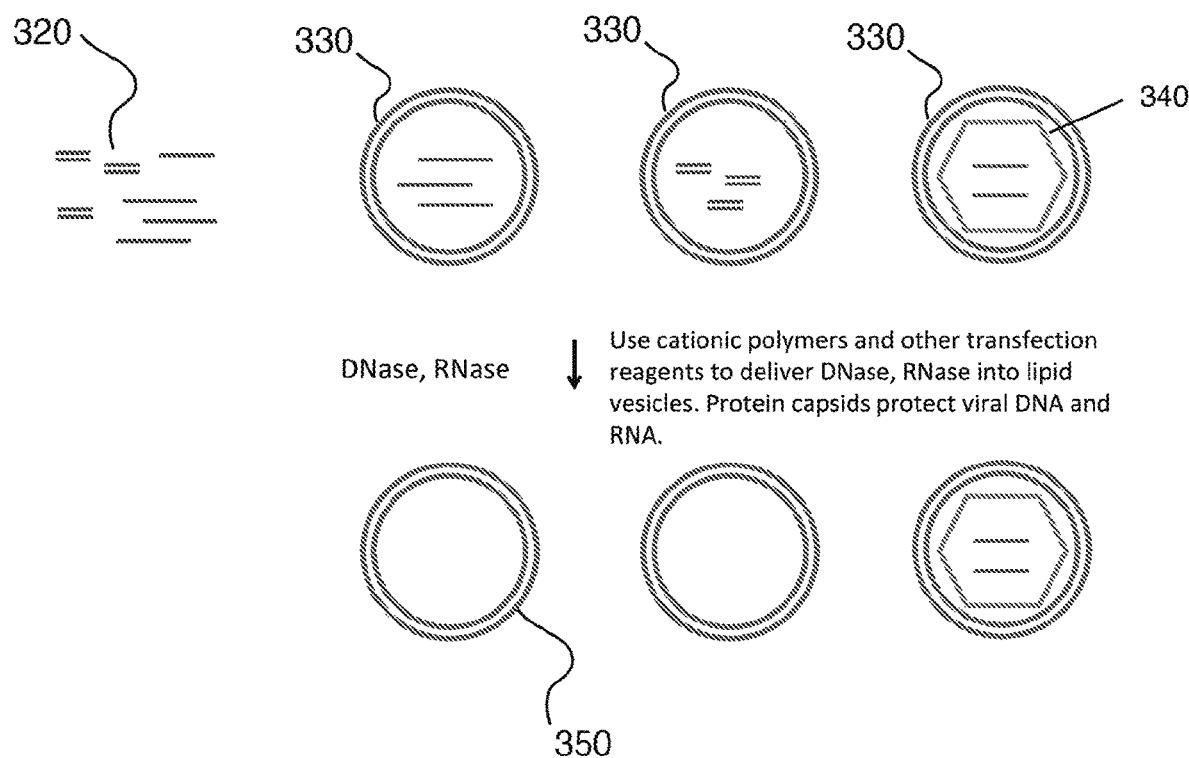
FIG. 6 depicts an example embodiment in which viral nucleic acids in protein capsids are protected from degradation by DNase and RNase, while naked nucleic acids and nucleic acids in exosomes or apoptotic bodies can be degraded by DNase and RNase.

Some embodiments of the methods and compositions provided herein include enriching a sample for a viral nucleic acid contained in a protein capsid. In some embodiments, a sample can include a protein capsid containing a viral nucleic acid. In some embodiments, the sample can also include target nucleic acids not contained in a viral capsid or other type of proteinaceous shell. In some embodiments, the target nucleic acids can be contained in a vesicle, such as an exosome, or an apoptotic body. Target nucleic acids can be selectively degraded in the sample by treating the sample with agents that deliver a nuclease, such as a DNase or an RNase to the target nucleic acid, but not to the viral nucleic acid. Examples of delivery agents include cationic polymers, such as transfection reagents. Non-target nucleic acids can be used to prepare a library of nucleic acids. As shown in FIG. 6, cell-free nucleic acids 320 including double-stranded and single-stranded nucleic acids, and vesicles 330 containing single-stranded nucleic acids, double stranded nucleic acids, or protein capsids 340 containing viral nucleic acids can be contacted with DNase and RNase using delivery agents which can enter the vesicles. Nucleic acids contained in protein capsids 340 are protected from digestion.

Preparation of Nucleic Acid Libraries

Some embodiments provided herein relate to preparing a library of nucleic acids. In some embodiments, a library of nucleic acids can be sequenced. In some such embodiments, target nucleic acids in a sample of polynucleotides can be selectively cleaved using methods and compositions provided herein. The cleaved target nucleic acids can be removed from the sample, and the remaining non-target nucleic acids can be used to prepare a library of nucleic acids. Examples of library preparation reagents include a transposon, a ligase, and a sequencing primer. In another embodiment, a library of nucleic acids can be prepared from a sample of polynucleotides, and target nucleic acids can be selectively cleaved and removed from the library using methods and compositions provided herein.

In some embodiments, a ligation-based library preparation method is used, such as TruSeq™ (Illumina, Inc., San Diego Calif.). Ligation-based library preparation methods often make use of an adaptor design which can incorporate an index sequence at the initial ligation step and often can be used to prepare samples for single-read sequencing, paired-end sequencing and multiplexed sequencing. For example, nucleic acids, such as fragmented nucleic acids or cell-free DNA, may be end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides. In some embodiments nucleic acid library preparation comprises ligating an adapter oligonucleotide. Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites such as sequences complementary to primers including universal sequencing primers, single end sequencing primers, paired end sequencing primers, and multiplexed sequencing primers.

In some embodiments, a transposon-based library preparation method is used such as Nextera™ (Epicentre, Madison, Wis.). Transposon-based methods may use in vitro transposition to simultaneously fragment and tag DNA in a single-tube reaction. This may allow incorporation of platform-specific tags and optional barcodes, and prepare sequencer-ready DNA libraries.

In some embodiments a nucleic acid library or parts thereof are amplified by PCR or other well-known methods. In some embodiments a sequencing method comprises amplification of a nucleic acid library. A nucleic acid library can be amplified prior to or after immobilization on a solid support, such as a solid support in a flow cell. Nucleic acid amplification includes the process of amplifying or increasing the numbers of a nucleic acid template and/or of a complement thereof that are present by producing one or more copies of the template and/or its complement. Amplification can be carried out by any suitable method. In some embodiments, the library may be amplified using primer sites in adaptor sequences, and sequenced using sequencing primer sites in the adaptor sequences. In some embodiments the adaptor sequences can include indexes to identify the source of the nucleic acids. The efficiency of subsequent amplification steps can be reduced by the formation of primer-dimers. To increase the efficiency of subsequent amplification steps, non-ligated single-stranded adaptors can be removed from ligation products.

Some embodiments provided herein can include sequencing a nucleic acid. Examples of sequencing technologies include sequencing-by-synthesis (SBS). In SBS, extension of a nucleic acid primer along a nucleic acid template is monitored to determine the sequence of nucleotides in the template. The underlying chemical process can be polymerization. In a particular polymerase-based SBS embodiment, fluorescently labeled nucleotides are added to extend a primer in a template dependent fashion such that detection of the order and type of nucleotides added to the primer can be used to determine the sequence of the template. One or more amplified nucleic acids can be subjected to an SBS or other detection technique that involves repeated delivery of reagents in cycles. For example, to initiate a first SBS cycle, one or more labeled nucleotides, DNA polymerase, etc., can be flowed into/through a hydrogel bead that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell before or after detection occurs. Washes can be carried out between the various delivery steps. The cycle can then be repeated n times to extend the primer by n nucleotides, thereby detecting a sequence of length n.

Some SBS embodiments include detection of a proton released upon incorporation of a nucleotide into an extension product. For example, sequencing based on detection of released protons can use an electrical detector and associated techniques that are commercially available. Examples of such sequencing systems are pyrosequencing such as a commercially available platform from 454 Life Sciences a subsidiary of Roche; sequencing using γ-phosphate-labeled nucleotides, such as a commercially available platform from Pacific Biosciences; and sequencing using proton detection, such as a commercially available platform from Ion Torrent subsidiary of Life Technologies.

Pyrosequencing detects the release of inorganic pyrophosphate (PPi) as particular nucleotides are incorporated into a nascent nucleic acid strand. In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero mode waveguides (ZMWs). Another useful sequencing technique is nanopore sequencing. In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore.

In methods of isolating nucleic acids, amplification, and sequencing, various reagents may be used for nucleic acid isolation and preparation. Example reagents include, lysozyme; proteinase K; random hexamers; a polymerase such as I29 DNA polymerase, Taq polymerase, Bsu polymerase; transposase such as Tn5; primers, such as P5 and P7 adaptor sequences; ligase; deoxynucleotide triphosphates; buffers; and divalent cations.

Adaptors can include sequencing primer sites, amplification primer sites, and indexes. As used herein an "index" can include a sequence of nucleotides that can be used as a molecular identifier and/or barcode to tag a nucleic acid, and/or to identify the source of a nucleic acid. In some embodiments, an index can be used to identify a single nucleic acid, or a subpopulation of nucleic acids. In some embodiments, nucleic acid libraries can be prepared within a hydrogel on a flow cell device.

Kits

Some embodiments of the methods and compositions provided herein include kits. Some embodiments include a kit for selectively cleaving a target nucleic acid by recombinase-mediated cleavage. In some embodiments, the can include a single-stranded nucleic acid probe, a recombinase, and a first nuclease. Examples of recombinases include RecA, UvsX, RAD51, and derivatives thereof. Examples of the first nuclease include nuclease S1, mung bean nuclease, and a recombinant protein comprising a domain having nuclease activity and a single-stranded nucleic acid binding domain. In some embodiments, the kit can include a plurality of different single-stranded nucleic acid probes. In some embodiments, the single-stranded nucleic acid probe can contain a sequence complementary to a target nucleic acid, such as mitochondrial DNA, a repetitive element such as an interspersed repeat, a tandem repeat, and a long terminal repeat. In some embodiments, a kit can also include one or more components such as a polymerase, a single-stranded binding protein, a terminator nucleotide, a dUTP nucleotide, a second nuclease such as uracil DNA glycosylase, apurinic/apyrimidinic endonuclease, and DNA glycosylase endonuclease VII, and a reagent to remove cleaved target nucleic acids from non-target nucleic acids, such as SPRI beads.

Some embodiments include reagents for preparing a library of single-stranded nucleic acid probes. Example reagents for preparing a library of single-stranded nucleic acid probes can include one or more of an enzyme which nicks double-stranded DNA such as DNase I, an enzyme which creates gaps in nicked double-stranded DNA such as exonuclease III, a reagent to denature double-stranded DNA to single-stranded species, and a reagent to remove double-stranded DNA from single-stranded DNA. More examples reagents for preparing a library of single-stranded nucleic acid probes can include one or more of a plurality of degenerate primers, and a thermophilic polymerase. In some embodiments, the degenerate primers include a purification tag, such as biotin. In some embodiments, the degenerate primers include a cleavable linker, such as a poly-U sequence that can be used to remove the purification tag from products generated from the degenerate primers. In some embodiments, a kit can include a substrate to capture products generated from the degenerate primers, such as beads, such as beads coated with streptavidin.

Some embodiments of the methods and compositions provided herein include a kit for selectively enriching a sample containing a target RNA and a non-target RNA. In some embodiments, a kit can include a single-stranded DNA probe containing a sequence complementary to a target RNA, an RNase H, and a DNase. In some embodiments, the kit can include a plurality of different single-stranded DNA probes. In some embodiments, the single-stranded DNA probe includes a sequence complementary to a sequence selected from the group consisting of ribosomal RNA, tRNA, and mRNA.

EXAMPLES

Example 1—Preparing a Library of Nucleic Acid Probes

Genomic DNA is obtained from a human fibroblast cell-line. The genomic DNA is amplified using a library of degenerate primers which each include a 5' biotin tag linked to the primer through a poly-U linker. The amplified products are captured on streptavidin beads, and the linker is cleaved using uracil DNA glycosylase. The amplified products are denatured to single-stranded nucleic acids, and fragmented by sonication. A library of human-specific single-stranded nucleic acid probes is prepared.

Example 2—Dehosting a Sample Containing Human and Non-Human DNA

A DNA sample is obtained from human blood. Human DNA is removed from the DNA sample by recombinase-mediated selective cleavage of the human DNA. Briefly, the DNA sample is mixed with the library of Example 1, a UvsX recombinase, a DNA polymerase, and nuclease S1. Non-human DNA is captured using SPRI beads, and cleaved human DNA is removed by washing the beads. A library of nucleic acids is prepared form the non-human DNA, and the library is sequenced.

Example 3—Depletion of Ribosomal and Globin RNA Using RNase H

A human RNA sample derived from a blood sample was hybridized with single-stranded DNA oligonucleotides targeting ribosomal RNA and globin mRNA sequences. RNA that had hybridized to the single-stranded DNA oligonucleotides were degraded with RNase H, and the single-stranded DNA oligonucleotides were degraded with DNase. Remaining RNA was reverse transcribed, a library of nucleic acids was prepared, and the library was sequenced. An example work flow is depicted in FIG. 5. The sequences were aligned to sequences in a database. Over 85% of the sequences obtained from RNA that had been treated with the single-stranded DNA oligonucleotides and RNase H were aligned to sequences in the database. In contrast, less than 12% of the sequences obtained from RNA that had been treated with the single-stranded DNA oligonucleotides and not with RNase H aligned to sequences in the database. Thus, treatment with the single-stranded DNA oligonucleotides and RNase H greatly increased the sensitivity of alignment.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of selectively cleaving a target nucleic acid in a sample comprising:
   (a) obtaining (i) a sample comprising a target nucleic acid and a non-target nucleic acid, wherein the target nucleic acid is double-stranded, and (ii) a plurality of random single-stranded nucleic acid probes capable of hybridizing to the target nucleic acid, wherein obtaining the plurality of random single-stranded nucleic acid probes comprises:
   generating the plurality of random single-stranded probes from a target nucleic acid source lacking the non-target nucleic acid;
   (b) contacting the target nucleic acid with the plurality of random single-stranded nucleic acid probes and a recombinase such that a plurality of D-loops in the target nucleic acid is formed; and
   (c) contacting the D-loops with a nuclease thereby cleaving the target nucleic acid.

2. The method of claim 1, further comprising: (d) removing the cleaved target nucleic acid from the non-target nucleic acid.

3. The method of claim 1, wherein step (b) comprises stabilizing the D-loops by contacting the D-loops with a polymerase, and extending the single-stranded nucleic acid probes.

4. The method of claim 3, further comprising a nucleic acid amplification reaction comprising the extending the single-stranded nucleic acid probes, wherein the nucleic acid amplification reaction is selected from an isothermal amplification reaction, and a PCR.

5. The method of claim 3, wherein the extension is performed in the presence of a terminator nucleotide.

6. The method of claim 3, wherein the extension is performed in the presence of a limiting amount of at least one type of nucleotide, and wherein the limiting amount is sufficient to inhibit a rate of the extension.

7. The method of claim 3, further comprising degrading the nucleic acids extended from the single-stranded nucleic acid probes.

8. The method of claim 7, further comprising incorporating dUTP nucleotides into the extended nucleic acids, and contacting the extended nucleic acids with a nuclease selected from the group consisting of uracil DNA glycosylase, apurinic/apyrimidinic endonuclease, and DNA glycosylase endonuclease VII.

9. The method of claim 1, wherein step (b) further comprises contacting the D-loops with a single-stranded binding protein.

10. The method of claim 1, wherein the recombinase is selected from the group consisting of RecA, UvsX, RAD51, and derivatives thereof.

11. The method of claim 10, wherein the recombinase comprises an UvsX recombinase.

12. The method of claim 1, wherein the nuclease is a single-stranded specific endonuclease selected from a S1 nuclease, and mung bean nuclease.

13. The method of claim 1, wherein the sample comprises a plurality of target nucleic acids different from each other.

14. The method of claim 1, wherein the generating comprises fragmenting the target nucleic acid source.

15. The method of claim 1, wherein the generating comprises contacting the target nucleic acid source with a plurality of random oligonucleotides and a polymerase.

16. The method of claim 1, wherein the target nucleic acid is genomic DNA, and the non-target nucleic acid is prokaryotic nucleic acid or viral nucleic acid.

17. A method of dehosting a nucleic acid sample comprising a target nucleic acid and a non-target nucleic acid, wherein the target nucleic acid is double-stranded, comprising:
(a) obtaining a plurality of random single-stranded nucleic acid probes capable of hybridizing to the target nucleic acid, wherein the plurality of random single-stranded nucleic acid probes is generated from a target nucleic acid source lacking the non-target nucleic acid;
(b) contacting the nucleic acid sample with the plurality of random single-stranded nucleic acid probes and a recombinase such that a plurality of D-loops in the target nucleic acid is formed; and
(c) contacting the D-loops with a nuclease, thereby dehosting the target nucleic acid.

18. The method of claim 17, wherein step (a) further comprises generating the plurality of random single-stranded primers by (i) contacting the target nucleic source with a plurality of random oligonucleotides and a polymerase, or (ii) fragmenting the target nucleic source.

19. The method of claim 17, wherein step (b) further comprises stabilizing the D-loops.

20. The method of claim 19, wherein the stabilizing comprises (i) contacting the D-loops with a single-stranded binding protein, or (ii) contacting the D-loops with a polymerase.

* * * * *